United States Patent [19]

Uhm et al.

[11] Patent Number: 5,488,143
[45] Date of Patent: Jan. 30, 1996

[54] PROCESSES FOR THE CARBONYLATION OF METHANOL TO FORM ACETIC ACID, METHYL ACETATE AND ACETIC ANHYDRIDE

[75] Inventors: Sung J. Uhm, Seoul; Sung H. Han, Seongnam-shi; Jun W. Oh; Oh S. Joo, both of Seoul, all of Rep. of Korea

[73] Assignee: Korea Institute of Science and Technology, Seoul, Rep. of Korea

[21] Appl. No.: 183,344

[22] Filed: Jan. 19, 1994

Related U.S. Application Data

[60] Continuation-in-part of Ser. No. 175,577, Dec. 30, 1993, abandoned, which is a division of Ser. No. 81,107, Jun. 25, 1993, abandoned, and Ser. No. 174,263, Dec. 28, 1993.

[30]  Foreign Application Priority Data

Jun. 30, 1992 [KR] Rep. of Korea ............... 92-11524
Oct. 30, 1992 [KR] Rep. of Korea ............... 92-20188
Dec. 23, 1992 [KR] Rep. of Korea ............... 92-25281
Jul. 27, 1993 [KR] Rep. of Korea ............... 92-14265

[51] Int. Cl.$^6$ .......................... C07C 67/36; C07C 53/08; C07C 51/12
[52] U.S. Cl. .................... 560/232; 562/891; 562/608
[58] Field of Search ................... 560/232; 562/891, 562/608

[56]  References Cited

U.S. PATENT DOCUMENTS 3,717,670  2/1973  Schultz .................. 260/476 R
4,205,956  6/1980  Stedman .
4,959,498  9/1990  Luft et al. ................ 562/891
5,202,481  4/1993  Scates et al. ............. 562/608

FOREIGN PATENT DOCUMENTS 0335625  10/1989  European Pat. Off. .
0350635   1/1990  European Pat. Off. .
 247050   2/1926  United Kingdom .

*Primary Examiner*—Arthur C. Prescott
*Attorney, Agent, or Firm*—Oblon, Spivak, McClelland, Maier & Neustadt

[57]  ABSTRACT

The present invention provides an improved process for selectively producing acetic acid and/or methyl acetate by the gas phase carbonylation of methanol with carbon monoxide; an improved process for producing acetic anhydride directly from the methyl acetate; and a novel method for sustaining the life time of a carbonylation or a hydroformylation catalyst by pretreating the carbon monoxide or the synthesis gas to be used in carrying out the gas phase carbonylation or the hydroformylation.

52 Claims, No Drawings

PROCESSES FOR THE CARBONYLATION OF METHANOL TO FORM ACETIC ACID, METHYL ACETATE AND ACETIC ANHYDRIDE

REFERENCE TO RELATED APPLICATIONS

This application is a continuation-in-part of U.S. Ser. No. 08/175,577 filed on Dec. 30, 1993, now abandoned, which is, in turn, a divisional application of U.S. Ser. No. 08/081, 107 filed on Jun. 25, 1993, now abandoned; and, U.S. Ser. No. 08/174,263, which was filed on Dec. 28, 1993.

FIELD OF THE INVENTION

The present invention relates to a process for selectively preparing acetic acid and/or methyl acetate by carbonylating methanol with carbon monoxide and a process for producing acetic anhydride from the methyl acetate obtained from said carbonylation. Further, the present invention relates to a process for pretreating carbon monoxide or syn gas to be used in said carbonylation or in a hydroformylation process.

BACKGROUND OF THE INVENTION

Acetic acid and acetic anhydride have long been used as basic chemicals for industrial purposes such as solvents, raw materials and intermeidates for various reaction products.

Acetic acid has been traditionally produced by oxidation of ethanol or acetaldehyde prepared by Wacker process starting from ethylene or low boiling raffinates produced in a petroleum process. These oxidation processes are being replaced by a carbonylation process which reacts methanol with carbon monoxide employing a rhodium catalyst in the presence of methyl iodide in liquid phase. However, the liquid phase carbonylation process has been found to have various critical deficiencies including the continuous loss of the expensive catalyst and the high corrosion problem stemming from the liquid phase reaction mixture which entail extremely high construction, maintenance and production costs.

Acetic anhydride can be produced by reacting one molecule of the ketene intermediate obtained by the pyrolysis of acetic acid with another molecule of acetic acid. This process has been also obsoleted by the liquid phase carbonylation process of converting methyl acetate with carbon monoxide in the presence of a rhodium catalyst and the methyl iodide promoter, as will be further discussed below.

Methyl acetate, which has been generally prepared by the esterification of acetic acid with methanol, has not been widely used as a chemical raw material due to its high production cost, despite its large potential as a key intermediate to numerous industrially important chemicals including acetic anhydride, ethanol, alkyl acetates, vinyl acetate monomer and the like.

In order to overcome the various problems associated with the liquid phase carbonylation of methanol to produce acetic acid, therefore, various proposals have been made to provide a process for producing acetic acid in a gas phase. For example, the processes disclosed in European Patent Publication No. 0 069 514 A2 assigned to Toyo Engineering Corporation, German DE 33 23 654, and *Ind. Chem. Prod., Res. Dev.*, 22, 436(1983) and *Chemistry Letters.*, 895(1987) relate to the gas phase production of acetic acid by a nickel-catalyzed carbonylation of methanol; however, none of these processes has proven to be commercially viable due to various problems.

European Patent Publication No. 0 335 625 A2 provides a process for producing acetic acid by employing a nickel/rhodium catalyst supported on active carbon at 188° C. In this process, a mixture of $CO/H_2(1:2)$ gas is introduced under a pressure of 9 arm, with the ratio of methanol to methyl iodide being 100:19.1 and the LHSV of the feed being 1. However, this process results in a low yield of 9.7%. In addition, nickel is apt to be vaporized from the catalyst beds during the reaction, thereby shortening the life time of the catalyst.

U.S. Pat. Nos. 3,717,670(to Hockman) and 3,689,533 (to Schultz) offer processes for producing acetic acid in a heterogeneous gas phase using a rhodium catalyst. These patents teach that the conversion of methanol and the yield of acetic acid may be improved by mixing the Rh catalyst with a metallic component. However, according to these patents, the methanol conversion, the selectivity and the yield of acetic acid are no more than 78.5%, 58% and 45.5%, respectively, under the most preferred reaction conditions: i.e., a reaction temperature of 285° C. and pressure of 200 psi, with the molar ratio of $CH_3I:CH_3OH:CO$ being 1:12.3:26.2.

Japanese Laid-open Patent Publication No. Sho 48-80511 describes a gas phase process for preparing acetic acid wherein a rhodium compound is employed as a catalyst and a small amount of cobalt, nickel or iron salt and/or aluminum, copper, titanium, mercury or lithium salt is added as a co-catalyst. In this method, methanol, carbon monoxide and methyl iodide are introduced at a rate of 169 g/hr, 224 g/hr and 27 g/hr, respectively, using the catalyst prepared by supporting 0.43 g of $RhCl_3.4H_2O$, 0.43 g of $NiCl_2$, 0.44 g of $AlCl_3$ and 0.43 g of LiCl on 25 g of active carbon; and the reaction is carried out at 230° C. under 220 psi. However, this process gives an acetic acid yield of 71%.

U.S. Pat. No. 4,918,218 to Mueller, et al. and German Patent No. 36 06 169 relate to a gas phase process using a nickel/palladium complex catalyst system and a process using a cobalt catalyst supported on zeolite, respectively. However, neither process has been regarded as commercially viable in view of their low reactivity, conversion and selectivity to acetic acid.

As a separate but related matter, among the various problems that exist in the afore-mentioned gas phase carbonylation processes to produce acetic acid, the most critical impediment to their commercialization has been the short life time of the expensive(e.g., rhodium) catalyst due to its contamination by impurities present in the feed gas, i.e., CO.

As a matter of fact, the task of dealing with the contamination of catalysts is a pervasive one throughout the chemical industry as numerous chemicals are prepared by catalytic reactions using an industrial gas such as synthesis gas(CO/$H_2$) and carbon monoxide. Representative of such reactions include hydroformylation and carbonylation of various reactants to produce, e.g., acetic acid and acetic anhydride, as discussed above. In these reactions, expensive noble metals, including rhodium, are generally used as a catalyst.

The afore-mentioned industrial gases can be manufactured by various known processes. During the processes, various impurities, especially iron carbonyl compounds, are formed as the gases come in contact with iron. Also, when they are stored in an iron vessel at a room temperature for a substantial period of time, a significant amount of iron carbonyl compounds may be formed.

Said iron carbonyl compounds have been found to cause serious problems in carrying out the above catalytic reactions as they tend to accumulate on the active surface of the catalyst and poison the catalyst rapidly. The iron carbonyl compounds, even in a minor amount, may degrade the catalyst performance, including its reactivity and selectivity, after a repeated use thereof. Accordingly, unless and until a commercially feasible solution is found to remove the catalyst contamination problem, there may be no practicable alternative to, e.g., the existing liquid phase process for the production of acetic acid discussed above.

Turning now to prior art methods of producing acetic anhydride, U.K. Patent No. 1 523 346 teaches a process for preparing acetic anhydride from methyl acetate and carbon monoxide in a liquid phase reaction in the presence of a metallic catalyst such as ruthenium, rhodium, palladium, osmium, iridium and platinum. In accordance with this process, starting materials are preferably used in anhydrous form, but they may contain up to 25% of methanol and 5% of water. In this process, since the water present in the reaction system tends to cause the formation of acetic acid, it is vitally important to remove the water from the reactants in order to obtain acetic anhydride in a higher yield or selectivity.

To solve the problem of removing water encountered in the preparation of acetic anhydride, therefore, European Patent Publication No. 0 087 870 A2 proposes a method comprising the steps of esterifying the produced acetic acid with methanol followed by dehydrating, carbonylating and separating the resulting product. Specifically, this process comprises esterifying methanol with recycled acetic acid to obtain a mixture of methyl acetate, methanol and water and removing the water from the esterification product; further dehydrating the methyl acetate by, e.g., injecting acetic anhydride and carbonylating the dehydrated methyl acetate with CO in a liquid phase to produce simultaneously acetic arthydride and acetic acid depending on the contents of water and methanol in the reactants; separating an overhead fraction containing the carbonylation feed and halide promoter, an intermediate fraction containing acetic acid and acetic arthydride, and a lower fraction containing the carbonylation catalyst components from the reaction mixture; recycling the overhead fraction and the lower fraction to the carbonylation reactor; further separating the intermediate fraction into acetic acid and acetic anhydride; recycling the separated acetic acid to the esterification reactor; and, finally, recovering the acetic anhydride.

Not only is the above process highly complicated and costly, it is very difficult to remove water after the esterification step. For example, when the esterification is carried out using methanol and acetic acid in a molar ratio of 2:1, 57.5% by weight of methyl acetate, 27.9% by weight of methanol and 13.6% by weight of water are produced. The resulting water must be removed by azeotropic distillation of water and methanol. Thereafter, another step is required to separate methanol from water.

In addition to the water removal problem, there exists another cost-related deficiency in the above process for the preparation of acetic anhydride: that is, methyl acetate is prepared by esterifying acetic acid with methanol and the methyl acetate so produced is used as the starting material for the next carbonylation step wherein said acetic anhydride (and acetic acid) is produced, which further increases the overall production cost of acetic anhydride.

SUMMARY OF THE INVENTION

Accordingly, it is an object of the invention to provide a process for selectively producing acetic acid by the gas phase carbonylation of methanol with carbon monoxide, said carbon monoxide optionally in admixture of hydrogen, using a Rh catalyst and a halide co-catalyst wherein all or substantially all of the methyl acetate separated from the production mixture together with the co-catalyst is recycled.

It is another object of the invention to provide a process for selectively producing methyl acetate by the gas phase carbonylation of methanol with carbon monoxide, said carbon monoxide optionally in admixture of hydrogen, using a Rh catalyst and a halide co-catalyst under milder carbonylation conditions and a higher GHSV(Gas Hourly Space Velocity) of methanol wherein all of the co-catalyst and a fraction of the methyl acetate produced, e.g., as an azeotropic amount, is recycled.

It is a further object of the present invention to provide a process for economically producing acetic anhydride directly from the methyl acetate, accompanied by the co-catalyst used therewith, produced in accordance with the inventive gas phase carbonylation process discussed above.

It is a still further object of the invention to provide a novel method for sustaining the active life time of a carbonylation or a hydroformylation catalyst by pretreating the carbon monoxide or the synthesis gas to be used in carrying out the gas phase carbonylation or the hydroformylation.

In accordance with one aspect of the present invention, there is provided a gas phase process for the selective production of acetic acid, which comprises:

(a) carbonylating methanol in a gas phase with carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst to produce a mixture of acetic acid and methyl acetate;

(b) separating said methyl acetate and the co-catalyst from the production mixture while recovering the acetic acid; and (c) recycling all or substantially all of the separated methyl acetate together with the co-catalyst into the carbonylation reactor.

In accordance with another aspect of the present invention, there is provided a process for selectively producing methyl acetate, which comprises:

(a) carbonylating methanol in a gas phase with carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under milder carbonylation conditions and a higher GHSV of methanol to produce a mixture of acetic acid and methyl acetate;

(b) separating from the production mixture in a distillation column the acetic acid as a high boiling fraction thereof, a mixture of the co-catalyst and a minor portion, e.g., an azeotropic amount, of the methyl acetate as a low boiling fraction thereof, and the remaining major portion of the methyl acetate as an intermediate boiling fraction thereof;

(c) recycling the separated mixture of the co-catalyst and the minor portion of the methyl acetate to the carbonyltion reactor; and (d) recovering the separated acetic acid and the separated remaining major portion of the methyl acetate, respectively.

In accordance with a further aspect of the present invention, there is provided a process for economically producing acetic anhydride, which comprises:

(a) carbonylating methanol in a gas phase with carbon monoxide in a first carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under milder carbonylation conditions and at a higher GHSV of methanol to produce a mixture of acetic acid and methyl acetate;

(b) separating from the production mixture in a distillation column the acetic acid as a high boiling fraction thereof, and a mixture of the methyl acetate and the co-catalyst as a low boiling fraction thereof;

(c) removing, optionally, a portion of the co-catalyst from the low boiling fraction and recycling it to the first carbonylation reactor;

(d) introducing the methyl acetate and all or the remaining portion of the co-catalyst into a second carbonylation reactor;

(e) carbonylating the methyl acetate, in either a liquid or a gas phase, with carbon monoxide in the second carbonylation reactor in the presence of a catalyst and the co-catalyst to produce a mixture containing acetic anhydride; and (f) recovering the acetic anhydride from the mixture while separating and recycling the co-catalyst to the first carbonylation reactor.

In accordance with a still further aspect of the present invention, there is provided a method for pretreating an industrial gas containing metallic carbonyl compounds, which comprises contacting said industrial gas with a halogen to remove said metallic carbonyl compounds contained therein.

DETAILED DESCRIPTION OF THE PREFERRED EMBODIMENTS

A. Pretreatment of Carbon Monoxide or Syn Gas

As previously stated, an industrial gas, i.e., carbon monoxide gas of syn gas, may contain as impurities metallic (e.g., iron) carbonyl compounds. These impurities tend to contaminate or poison the catalyst employed in an oxo process or a carbonylation process rather rapidly, rendering the process commercially ineffective.

In accordance with the present invention, it has been found that such catalyst contamination problem can be effectively removed by treating the syn gas of carbon monoxide, prior to its exposure to the hydroformylation or carbonylation catalyst, with a halogen gas.

Specifically, an industrial gas, e.g., CO, containing metallic carbonyl compounds, is fed into a purification column wherein a halogen, for example, iodine, is introduced. The amount of iodine to be used is determined as a function of the flow rate of the feed gas and the column temperature. Said iodine is introduced into the column in a molar amount ranging from 0.1 to 1000, more preferably from 0.5 to 100, and, most preferably, from 1 to 10 times the metallic content in the feed gas. Several trays may be installed in the column to ensure good mixing between the feed gas and the iodine. The column is maintained at a temperature, for example, in a range from 150° C. to 200° C., to allow the metallic carbonyl impurities to react completely with the halogen gas. The metallic halides, e.g., iron and/or nikel iodide, are sent to an adsorption column and adsorbed onto the adsorbent therein, producing the desired purified feed gas. Examples of the adsorbent which may be used in the present invention include active carbon, clay, alumina, silica, silica-alumina, zeolite and other adsorbents commonly used in the art. The feed gas thus purified is transferred to, e.g., a carbonylation reactor.

The industrial gas treated in accordance with the present invention may contain, if any, the metallic carbonyl compounds only in a negligible amount, e.g., 1 ppb or less, which is rather difficult to detect by a conventional analysis method. Consequently, the problem of the catalyst poisoning and reactivation encountered in an Oxo or a carbonylation process can be effectively resolved.

B. Selective Production of Acetic Acid and/or Methyl Acetate

In accordance with another aspect of the present invention, a process for the selective production of acetic acid and/or methyl acetate is accomplished by controlling the reaction conditions in the gas phase carbonylation of methanol with carbon monoxide in the presence of a rhodium catalyst and a halide co-catalyst(which is sometimes called a promoter).

Said carbon monoxide is preferably pretreated with a halogen gas as described previously; and, if desired, may be introduced together with an appropriate amount of hydrogen gas to enhance the selectivity and yield of acetic acid or methyl acetate.

The carbon monoxide may be introduced at a pressure near or slightly higher than the reaction pressure, e.g., 13 arm and at a temperature preheated to a desired reaction temperature, e.g., 250° C.; and employed in a molar ratio of methanol to carbon monoxide ranging from 1:0.1 to 1:100, more preferably 1:0.5 to 1:50, most preferably 1:0.8 to 1:3.

Similarly, methanol is preferably preheated and vaporized to the desired reaction temperature and pressure prior to its introduction into the reaction system.

B.1. Selective production of acetic acid

In accordance with the present invention, when it is desired to produce acetic acid primarily, the selectivity to acetic acid is enhanced by adjusting the reaction conditions: i.e., the reaction temperature to range from room temperature to 500° C., more preferably from 150° to 300° C., most preferably from 200° to 280° C.; the reaction pressure to range from atmospheric pressure to 300 arm, more preferably from 5 to 30 arm, most preferably from 10 to 20 arm; and the contact time of the reactants with the catalyst as inversely represented by the GHSV of methanol to range from 1 to 100,000 $hr^{-1}$, more preferably from 100 to 10,000 $hr^{-1}$, and most preferably from 300 to 5,000 $hr^{-1}$.

In accordance with a preferred embodiment of the present invention, it has been found that the selectivity to acetic acid can be maintained at a level of 99% or higher by initially adding an appropriate amount of methyl acetate (e.g., about 10 mol % based on the methanol used) to the feed stream of methanol, and, thereafter, separating and recycling the methyl acetate together with the co-catalyst, e.g., methyl iodide, used.

In accordance with another preferred embodiment of the present invention, hydrogen may be beneficially added in an amount up to 50% by volume to the feed gas, i.e., carbon monoxide. In the case of conventional liquid phase reactions, when hydrogen is present in carbon monoxide, various side reactions may occur, thereby lowering the reaction efficiency. However, in the gas phase catalytic reaction of the present invention, the presence of hydrogen in the reaction system in fact considerably enhances the conversion of methanol and selectivity to acetic acid(or methyl acetate depending on the reaction conditions employed). Also, the ability to use a mixture of hydrogen and carbon monoxide has an added advantage since it obviates the need to prepare carbon monoxide free from hydrogen.

In a further preferred embodiment of the present invention, water may be added in the reaction system, particularly to the recycling stream of the methyl acetate, up to 20 mol % based on the methanol used, in order to improve the selectivity to acetic acid. However, if a higher yield of methyl acetate is desired, the water content in the reactants should be maintained at a lowest possible level so as to inhibit the formation of acetic acid.

B.2. Selective production of methyl acetate

On the other hand, when it is desired to produce methyl acetate rather than acetic acid, the selectivity to the desired methyl acetate can be increased in a simple manner in accordance with the present invention. That is, the carbonylation is carried out at a shorter contact time of the reactants with the catalyst as inversely represented by a GHSV of methanol ranging from 1 to 100,000 $hr^{-1}$, more preferably from 500 to 50,000 $hr^{-1}$ and most preferably from 1,000 to 10,000 $hr^{-1}$, and at milder reaction conditions: i.e., a lower pressure ranging from 1 to 300 atm, more preferably from 5 to 25 atm and most preferably from 8 to 15 arm; and a lower reaction temperature ranging from room temperature to 500° C., more preferably from 100° to 300° C. and most preferably from 150° to 270° C. to obtain methyl acetate in a higher yield.

As stated previously, the injection of an appropriate amount of hydrogen(e.g., about 10 mol % based on the carbon monoxide used) in the feed stream of carbon monoxide improves the conversion of methanol and the selectivity to methyl acetate under the adjusted reaction conditions.

As an exemplary embodiment, carbonylation of methanol with carbon monoxide can be carried out by using $RhCl_3$+$IrCl_3$ as the catalyst and $CH_3I$ as the co-catalyst at the reaction temperature of 255° C. and the reaction pressure of 200 psi. Said methanol is passed through the catalyst beds at a GHSV of 2500 $hr^{-1}$ to produce 82 mol % of methyl acetate and 18 mol % of acetic acid. The production mixture together with the methyl iodide is then sent to a distillation column to separate: said acetic acid and water, if any, as the bottoms product; almost the entire amount of the methyl iodide and an azeotropic amount of the methyl acetate as the light end product of the distillation column(wherein the azeotropic composition of $CH_3I$:$CH_3COOCH_3$ is 94.2 mol %:5.8 mol % at the boiling temperature of 42.1° C.), which are recycled to the carbonylation reactor; and the remaining major portion of the methyl acetate as an intermediate fraction of the distillation column. The methyl acetate so recovered is essentially dry, which is suitable for use in producing, e.g., an alkyl acetate.

B.3. Catalyst system

The rhodium catalyst for use in carrying out the gas phase carbonylation of methanol in accordance with the present invention comprises a rhodium compound and a second metallic component selected from the group consisting of an alkali metal, an alkaline earth metal, a transition metal and a mixture thereof; and may be prepared by depositing or impregnating a solution of the rhodium compound dissolved in water or an organic solvent, e.g., an alcohol, on an inert supporting material together with the second metallic compound, calcining the resultant at a temperature ranging from 200° to 500° C. The inert supporting material which may be used in preparing the catalyst includes active carbon, clay, alumina, silica, silica-alumina, alumina-phosphate, alumina-silica-phosphate, magnesia, zirconia and the like.

Any of the rhodium compounds, which are soluble in water or an organic solvent and can be calcined at the temperature range of 200° to 500° C., may be used. Representative of such rhodium compounds are: $RhX_3$, $RhX_3 \cdot 3H_2O$, $Rh_2(CO)_4X_2$, $[Rh(CO)X_4]Y$, $Rh_2(CO)_8$, $Rh(NO_3)_3$, $[Rh(CO)_2X_2]Y$, $Rh_2O_3$, $Rh(CH_3COO)_3$, $[Rh(C_2H_4)_2X]_2$, $Rh[(C_6H_5)_3P]_2(CO)X$, Rh metal, $RhX[(C_6H_5)_3P]_2(CH_3X)_2$, $Rh(SnX_3)[(C_6H_5)P]_3$, $RhX(CO)[(C_6H_5)_3Q]_2$, $(R_4Z)[Rh(CO)_2X]_2$, $(R_4Z)_2[Rh(CO)X_4]$, $RhX[(C_6H_5)_3P]_3$, $RhX[(C_6H_5)_3P]H_2$, $[(C_6H_5)_3P]_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group. Preferably, $RhCl_3 \cdot 3H_2O$ or $Rh(NO_3)$ is used.

The rhodium compound may be employed in an amount of 0.01 to 20% by weight, more preferably 0.1 to 10%, most preferably 0.3 to 5% by weight of Rh based on the amount of the supporting material. The transition metal compound may be added in an amount of 1 to 1000 mol %, more preferably 10 to 500 mol %, most preferably 30 to 300 mol %, based on the amount of rhodium. The alkali metal or the alkaline earth metal compound may be added in an amount of 1 to 2,000 mol %, more preferably 50 to 1000 mol %, most preferably 200 to 800 mol %, based on the amount of rhodium.

The alkali metal which may be employed as the second component in the rhodium catalyst includes Li, Na, K, Rb, Cs and Fr.

The alkaline earth metal which may be employed as the second component includes Be, Mg, Ca, Sr, Ba and Ra.

The transition metal which may be employed as the second component includes Co, Ru, Pd, Pt, Os, It, Ni, Mn, Re, Cr, Mo, W, V, Nb, Ta, Ti, Zr and Hr.

The carbonylation catalyst according to the present invention is easily prepared by adding at least one of the second metallic compounds such as $CoCl_2$, $RuCl_3$, $PdCl_2$, $PtCl_2$, $OsCl_3$, $ITCl_3$, $NiCl_2$, $MnCl_2$, $ReCl_5$, $CrCl_3$, $MoCl_3$, $WCl_6$, $VCl_3$, $NbCl_5$, $TaCl_5$, $TiCl_4$, $ZrCl_4$, $HfCl_4$, LiI, NaI, KI, RbCl, $BeCl_2$, $MgCl_2$, $CaCl_2$, $SrCl_2$, $BaCl_2$ and the like in a specified amount to a rhodium compound supported on the inert material.

The inventive gas phase process for selectively producing acetic acid and/or methyl acetate is carried out by using a halide co-catalyst in the presence of the rhodium catalyst.

The halide compound which may be employed as the co-catalyst includes: $CH_3I$, $CH_3Br$, $CH_3Cl$, $I_2$, $Br_2$, $Cl_2$, HI, HBr, HCl and the like. Among them, $CH_3I$ is preferred.

The halide co-catalyst may be employed in a molar ratio of the co-catalyt per mole of the methanol used ranging from 0.001 to 5, more preferably from 0.01 to 1 and most preferably from 0.05 to 0.15.

C. Production of Acetic Anhydride

In accordance with a further aspect of the present invention, acetic anhydride can be synthesized directly from the methyl acetate obtained in accordance with the carbonylation process of the present invention, described in B.2 above.

As described above, in the first carbonylation, methyl acetate may be produced in a high selectivity, e.g., 82% by a simple adjustment of the reaction conditions and by using a suitable catalyst, e.g., $RhCl_3+IrCl_3$ on active carbon. From the reaction mixture, methyl acetate and the co-catalyst can easily be separated from the rest of the mixture as a low boiling fraction in a distillation column. The separated mixture of the methyl acetate and the co-catalyst, either in its entirety or a portion thereof, is introduced into a second carbonylation reactor, which may be operated either in a gas phase or a liquid phase, to obtain acetic anhydride. In the second carbonylation reactor, the methyl acetate is carbonylated by the reaction with carbon monoxide freshly introduced, in the presence of a catalyst and the co-catalyst. It is important to note that the essentially dry methyl acetate obtainable from the first carbonylation process of the present invention is beneficially employed in the second carbonylation process to thereby obviate the costly drying process required in the prior art process of producing methyl acetate from the esterification of acetic acid with methanol.

After the second carbonylation reaction, the co-catalyst is separated from the acetic anhydride produced and recycled to the first carbonylation reactor for reuse.

The second carbonylation of methyl acetate may be conducted in a gas phase in the presence of the same rhodium catalyst and the same co-catalyst as described in B.2 or B.3 above; and carried out at a temperature ranging from 100° to 500° C., more preferably from 150° to 300° C., and most preferably 200° to 280° C., at a reaction pressure ranging from atmospheric pressure to 500 atm, more preferably from 5 to 25 arm, and most preferably from 10 to 20 atm, and at a GHSV of methyl acetate from 1 to 100,000 $hr^{-1}$, more preferably from 10 to 10,000 $hr^{-1}$ and most preferably ranging from 100 to 2000 $hr^{-1}$. The halide co-catalyst, in particular $CH_3I$, may be introduced into the reactor in a molar ratio of the co-catalyst per mole of methyl acetate ranging from 0.001 to 5, more preferably from 0.01 to 5 and most preferably from 0.05 to 0.15.

Carbon monoxide pretreated as described above can be employed in a molar ratio of methyl acetate to carbon monoxide ranging from 1:0.1 to 1:100, more preferably from 1:0.5 to 1:50, most preferably from 1:0.8 to 1:3.

On the other hand, when the second carbonylation is carried out in a liquid phase, it may be conducted in the presence of a noble metal catalyst, and a promoter and/or a ligand, as described in, e.g., U.K. Patent Nos. 1,468,940 and 1,523,346, which are incorporated herein by reference. Specifically, the noble metals which may be employed in the catalyst are those of Group VIII; and rhodium is preferred. Representative members which may be employed as the promoter include: organic cations, Group IA metals having an atomic weight greater than 5, Group IIA, IIIA, IVB or VIB metals, the non-noble metals of Group VIII, and the lanthanide and the actinide groups of metals; and Li, Mg, Ca, Ti, Cr, Fe, Ni and Al and preferred.

The catalyst and the promoter may be used in their elemental forms, e.g., as finely divided or powdered metals, or they may be employed as compounds of various types, both organic and inorganic, which are capable of effectively introducing the element .into the reaction system.

The compounds may include oxides, hydroxides, halides (e.g., bromides), and oxides, oxyhalides, hydrides, alkoxides, and the like. The noble metal compounds used as the catalyst are preferably rhodium compounds such as those listed in B.3 above, and, particularly, rhodium acetate. The compounds which may be employed as the promoter are preferably LiI, LiOAc, LiCl, PPNI(i.e., $Ph_3P=N^+=PPh_3.I^-$), zirconyl diacetate and a tetraammonium salt, more preferably LiI, LiOAc and PPNI; and the ligand may include phosphine, amine, antimony and tin compound ligands, preferably, the phosphine and the amine ligands.

In the liquid phase carbonylation process, the noble metal compound may be employed in an amount ranging from 0.0001 to 50 mol %, more preferably 0.001 to 10 mol %, and most preferably 0.01 to 1 mol %, based on the molar amount of methyl acetate; the promoter may be employed in an amount ranging from 0.01 to 200 mol %, more preferably 0.1 to 50 mol %, and most preferably 1 to 10 mol % based on the moles of methyl acetate; and the ligand may be employed in an amount ranging from 1 to 10,000 mol %, more preferably 10 to 1000%, and most preferably 50 to 500% based on the molar amount of the catalyst, e.g., rhodium, used.

Into, e.g., an autoclave reactor, the methyl acetate and an appropriate amount of the co-catalyst(see U.K. Patent No. 1 468 940, Examples 1 to 5) recovered from the first carbonylation, a metal catalyst, a promoter and/or a ligand are charged, and carbon monoxide is introduced thereto. The reaction may be carried out at a temperature ranging from room temperature to 500° C., more preferably 50° to 300° C., most preferably 150° to 200° C.; and at a pressure ranging from 1 to 500 atm, more preferably 10 to 300 atm; and most preferably 20 to 100 atm. The carbonylation reaction is preferably carried out in a substantial absence of water to avoid the production of acetic acid as a byproduct. Carbon monoxide, preferably pretreated with a halogen as described above, is introduced into the reactor until the desired reaction pressure is reached and maintained.

The reaction mixture resulting from the second carbonylation may be separated, by way of a fractional distillation, into: an overhead fraction containing the co-catalyst and unreacted methyl acetate, if any; an intermediate fraction containing acetic anhydride and acetic acid, if any; and, a liquid residue containing the catalyst/the promotor and/or the ligand. The co-catalyst and the unreacted methyl acetate separated at the top of the distillation column are recycled to the first carbonylation reactor for reuse. Acetic anhydride and any amount of acetic acid produced are further separated from the intermediate fraction and recovered, respectively; and the liquid residue containing the catalytic components is recycled to the second carbonylation reactor.

As mentioned previously, in accordance with the present invention, the yields of the products can readily be controlled. Accordingly, methyl acetate can be obtained in a higher yield by adjusting the reaction conditions of the first carbonylation; and acetic anhydride can be obtained in sequence directly from the methyl acetate produced in the inventive first carbonylation process.

The following Examples are given for the purpose of illustration only and are not intended to limit the scope of the invention.

EXAMPLE 1

Carbon monoxide maintained at a room temperature and the pressure of 100 atm containing approximately 1 ppm of iron carbonyl compounds, predominantly in the form of $Fe(CO)_5$, was treated with iodine at a concentration of approximately 5 ppm in a purification column. About 10 $m^3$ of the gas so treated was passed through an adsorption column which was filled with active carbon and maintained at 200° C. Under a standard temperature and pressure, carbon monoxide (10$m^3$) thus treated was collected and then passed through a gas scrubber containing 1L of conc.

sulfuric acid to dissolve the remaining iron carbonyl compounds in the gas after the treatment. Concentration of the iron ion in the sulfuric acid was measured to be 0.01 ppm or less.

It should be noted that carbon monoxide employed in all of the following Examples given in this specification is pretreated with iodine in a manner similar to the procedure described in Example 1 above, unless specified otherwise.

EXAMPLE 2

$RhCl_3$ and LiI were supported on active carbon by impregnating a solution of $RhCl_3$ and LiI on the carbon such that 0.6% by weight of Rh based on the amount of the active carbon and 400 mol % of LiI based on the amount of Rh were supported thereon. The resulting material was then calcined at 300° C. to prepare the catalyst.

A reactor tube, made of titanium and having an inside diameter of 1.27 cm (0.5 inch) and a length of 40 cm, was charged with 5g of the catalyst. The reactor tube was filled with glass fiber, pretreated in a NaOH solution, at the top and the bottom ends thereof so as to form a catalyst bed of 10 cm in length therein; and, a thermowell having an outside diameter of 0.64 cm (0.25 inch) with a thermocouple was inserted in the center of the reactor tube. The reactor tube was oil jacketed so as to heat it with a heating medium. Methanol and carbon monoxide in a molar ratio of 1:2.3 were introduced into the reactor tube; and were allowed to react in the presence of 10 mol % of the co-catalyst, $CH_3I$, based on the amount of the methanol used at an inside temperature of about 240° C. under a pressure of 200 psi.

The conversion of methanol, and the yields of acetic acid and methyl acetate depending on the GHSV of methanol under the above conditions are shown in Table 1 below.

one of the streams had been treated by passing it through a column provided with iodine gas followed by an adsorption column packed with silica; and the other stream had not been so treated. After conducting the carbonylation by employing each of the non-treated (Experiment 1) and pretreated (Experiment 2) carbon monoxide gases for given periods, the yields of the products were measured at the GHSV of methanol of $600hr^{-1}$ and $5000hr^{-1}$, respectively. The results are shown in Table 2.

TABLE 2

| Experiment | Period | Methanol conversion (%) | Yield of acetic acid (%) | Yield of methyl acetate (%) |
|---|---|---|---|---|
| 1 | 70 days, at the GHSV of 600 | 80.3 | 33.1 | 57.2 |
| 2 | 75 days, at the GHSV of 5000 | 95.3 | 78.2 | 17.1 |

As can be seen from Table 2, when the carbonylating gas, i.e., carbon monoxide, is pretreated with iodine gas, the activity of the catalyst is maintained even after its using for a substantially long period of time.

EXAMPLE 4

This Example was carried out in accordance with the procedure as described in Example 2, except that the reaction temperature and pressure were changed to 233½° C. and 150 psi, respectively, in addition to the different values of GHSV. The results are shown in Table 3 below.

TABLE 1

| $GHSV^{1)}$ ($hr^{-1}$) | 660 | 887 | 1130 | 1379 | 1810 | 2168 | 2536 | 3333 | 3841 | 5598 |
|---|---|---|---|---|---|---|---|---|---|---|
| Methanol conversion (%) | 100 | 100 | 100 | 100 | 100 | 100 | 99 | 99 | 99 | 97 |
| Yield of acetic acid$^{2)}$ (%) | 92 | 90.5 | 89.6 | 83.9 | 89.3 | 87.4 | 85.2 | 76.0 | 74.0 | 66 |
| Yield of methyl acetate$^{3)}$ (%) | 4.3 | 3.0 | 3.4 | 6.9 | 9.2 | 9.8 | 12.0 | 19.0 | 25.5 | 27.0 |

$^{1)}$GHSV = Gas Hourly Space Velocity ($hr^{-1}$) of methanol: This is a measure of determining the amount of the reactant, i.e., methanol, in a gas phase passing through the catalyst beds per hour. The higher the GHSV, the shorter the contact time of the catalyst with the reactant becomes, rendering the amount of the reactant to be treated per hour larger.

$^{2)}$Yield of acetic acid = $\frac{\text{Mole of acetic acid produced}}{\text{Mole of methanol introduced}} \times 100$ $^{3)}$Yield of methyl acetate = $\frac{\text{Mole of methyl acetate produced} \times 2}{\text{Mole of methanol introduced}} \times 100$

EXAMPLE 3

This Example was carried out in accordance with the procedure as described in Example 2, except that two separate feed streams of carbon monoxide were employed:

TABLE 3

| GHSV ($hr^{-1}$) | 1207 | 1568 | 1735 | 2133 | 3293 | 3652 | 4149 |
|---|---|---|---|---|---|---|---|
| Methanol conversion (%) | 96.4 | 93.7 | 88.9 | 84.3 | 71.6 | 68.8 | 62.2 |
| Yield of acetic | 33.0 | 22.3 | 20.0 | 15.5 | 10.7 | 8.6 | 7.5 |

TABLE 3-continued

| | | | | | | | |
|---|---|---|---|---|---|---|---|
| acid (%) | | | | | | | |
| Yield of methyl acetate (%) | 63.0 | 64.8 | 64.8 | 63.6 | 60.1 | 54.5 | 49.5 |

As can be seen from Tables 1 and 3, even if an identical catalyst is used, the production ratio of methyl acetate to acetic acid can easily be adjusted under different reaction conditions. That is, the results from Example 4 show that methyl acetate can be produced in a higher selectivity and yield by adjusting the reaction conditions, i.e., by lowering the reaction temperature and pressure and shortening the contact time of the methanol with the catalyst.

EXAMPLE 5

This Example was carried out in accordance with the procedure as described in Example 2, except that a catalyst prepared by supporting 800 mol % of LiI on active carbon, with different GHSV values, was employed. The results are shown in Table 4 below.

TABLE 4

| GHSV ($hr^{-1}$) | 600 | 900 | 1200 | 1500 | 1800 | 2100 | 2400 | 2700 |
|---|---|---|---|---|---|---|---|---|
| Methanol conversion (%) | 100 | 100 | 100 | 100 | 100 | 100 | >99 | >99 |
| Yield of acetic acid (%) | 91.5 | 92.1 | 93.6 | 92.7 | 92.2 | 92.6 | 78.5 | 78.9 |
| Yield of methyl acetate (%) | 6.5 | 6.3 | 5.1 | 6.0 | 5.6 | 6.1 | 19.2 | 19.8 |

EXAMPLE 6

This Example was carried out as described in Example 2, except that a catalyst supported on active carbon and containing 1.8% by weight of Rh based on the amount of active carbon and 400 mol % of LiI based on the amount of Rh was employed, and the reaction temperature and the pressure were changed to 270° C. and 150 psi, respectively, in addition to the different values of GHSV. The results are shown in Table 5 below.

TABLE 5

| GHSV ($hr^{-1}$) | 1000 | 2000 | 3500 | 4800 |
|---|---|---|---|---|
| Methanol conversion (%) | 99.8 | 99.9 | 100 | 99.8 |
| Yield of acetic acid (%) | 94.8 | 83.3 | 75.1 | 68.6 |
| Yield of methyl acetate (%) | 5.0 | 16.1 | 22.5 | 30.2 |

EXAMPLE 7

This Example was carried out as described in Example 2, except that a catalyst supported on active carbon and containing 0.6% by weight of Rh based on the amount of the active carbon and 200 mol % of NaI based on the amount of Rh was employed, and the reaction temperature and the pressure were changed to 240° C. and 200 psi, respectively, in addition to the different values of GHSV. The results are shown in Table 6 below.

TABLE 6

| GHSV ($hr^{-1}$) | 1000 | 1568 | 1735 | 2133 |
|---|---|---|---|---|
| Methanol conversion (%) | 100 | 99.9 | 100 | 99.7 |
| Yield of acetic acid (%) | 82.0 | 57.4 | 38.8 | 31.1 |
| Yield of methyl acetate (%) | 17.1 | 42.1 | 60.0 | 67.9 |

EXAMPLE 8

This Example was carried out in the same manner as described in Example 2, except that a catalyst supported on active carbon and containing 0.6% by weight of Rh based on the amount of the active carbon and 200 mol % of KI based on the amount of Rh, together with the different values of GHSV, was employed. The results are shown in Table 7 below.

TABLE 7

| GHSV ($hr^{-1}$) | 1039 | 1795 | 2997 | 4017 |
|---|---|---|---|---|
| Methanol conversion (%) | 100 | 100 | 99.7 | 96 |
| Yield of acetic acid (%) | 94.8 | 80.0 | 50.1 | 30.1 |
| Yield of methyl acetate (%) | 5.1 | 19.9 | 48.9 | 60.5 |

EXAMPLE 9

This Example was carried out as described in Example 2, except that a catalyst supported on active carbon and containing 0.6% by weight of Rh based on the active carbon and mol % of $MgCl_2$ based on the Rh, together with the different values of GHSV, was employed. The results are shown in Table 8 below.

TABLE 8

| GHSV (hr$^{-1}$) | 2068 | 3417 | 4855 | 5754 |
|---|---|---|---|---|
| Methanol conversion (%) | 100 | 98.8 | 94.6 | 84.9 |
| Yield of acetic acid (%) | 89.9 | 66.6 | 43.1 | 30.0 |
| Yield of methyl acetate (%) | 8.8 | 30.6 | 49.6 | 52.3 |

EXAMPLE 10

This Example was carried out as described in Example 2, except that a catalyst supported on active carbon and containing 0.6% by weight of Rh based on the active carbon and 50 mol % of ItCl$_3$ based on the Rh was employed, and the reaction temperature was changed to 255° C., in addition to the different values of GHSV. The results are shown in Table 9 below.

TABLE 9

| GHSV (hr$^{-1}$) | 800 | 1200 | 1500 | 2000 | 2500 |
|---|---|---|---|---|---|
| Methanol conversion (%) | 99.0 | 100 | 99.7 | 99.9 | 99.8 |
| Yield of acetic acid (%) | 74.0 | 53.8 | 38.9 | 27.7 | 18.3 |
| Yield of methyl acetate (%) | 24.1 | 44.3 | 60.1 | 71.0 | 80.1 |

EXAMPLE 11

This Example was carried out as described in Example 2, except that a catalyst supported on active carbon and containing 0.6% by weight of Rh based on the active carbon and molt of PdCl$_2$ based on the Rh was employed; and the reaction temperature and the pressure were changed to 255° C. and 150 psi, respectively, in addition to the different values of GHSV. The results are shown in Table 10 below.

TABLE 10

| GHSV (hr$^{-1}$) | 1000 | 2000 | 3000 | 4000 |
|---|---|---|---|---|
| Methanol conversion (%) | 99.1 | 95.2 | 85.3 | 78.1 |
| Yield of acetic acid (%) | 54.5 | 28.5 | 16.1 | 13.2 |
| Yield of methyl acetate (%) | 43.5 | 65.5 | 67.8 | 63.7 |

EXAMPLE 12

This Example was carried out as described in Example 2, except that a catalyst supported on active carbon and containing 0.6% by weight of Rh based on the active carbon and molt of RuCl$_3$ based on the Rh was employed, and the reaction temperature was changed to 255° C., in addition to the different values of GHSV. The results are shown in Table 11 below.

TABLE 11

| GHSV (hr$^{-1}$) | 1800 | 3000 | 4200 |
|---|---|---|---|
| Methanol conversion (%) | 93 | 84 | 73 |
| Yield of acetic acid (%) | 22.3 | 10.9 | 0.8 |
| Yield of methyl acetate (%) | 68.8 | 71.4 | 61.8 |

EXAMPLE 13

This Example was carried out as described in Example 2, except that a catalyst supported on active carbon and containing 0.6% by weight of Rh based on the active carbon and 50 mol % of CoCl$_2$ based on the Rh was employed; and the reaction temperature was changed to 210° C., in addition to the changed values of GHSV. The results are shown in Table 12 below.

TABLE 12

| GHSV (hr$^{-1}$) | 1000 | 2000 | 3000 | 4000 |
|---|---|---|---|---|
| Methanol conversion (%) | 99.9 | 98.0 | 91.1 | 82.3 |
| Yield of acetic acid (%) | 45.0 | 32.3 | 19.9 | 12.3 |
| Yield of methyl acetate (%) | 53.8 | 64.6 | 70.1 | 68.9 |

EXAMPLE 14

This Example was carried out as described in Example 2, except that a catalyst supported on active carbon and containing 0.6% by weight of Rh based on the active carbon and molt of NiCl$_2$ based on the Rh was employed, and the reaction temperature was changed to 210° C., in addition to the different values of GHSV. The results are shown in Table 13 below.

TABLE 13

| GHSV (hr$^{-1}$) | 1000 | 2000 | 3000 | 4000 |
|---|---|---|---|---|
| Methanol conversion (%) | 100 | 95.0 | 90.2 | 79.3 |
| Selectivity to acetic acid (%) | 49.9 | 39.1 | 29.1 | 18.0 |
| Selectivity to methyl acetate (%) | 50.1 | 59.9 | 70.1 | 81.3 |

EXAMPLE 15

This Example was carried out employing the same catalyst as described in Example 2, except that a certain amount of hydrogen was mixed with the carbon monoxide.

While changing the ratio of carbon monoxide to hydrogen, the mixed gas of carbon monoxide and hydrogen was introduced together with methanol into the reactor under a pressure of 14.1 kg/cm$^2$(200 psi). At this time, the molar ratio of methanol to carbon monoxide was 1:1.6, the GHSV of methanol was maintained at 1500 hr$^{-1}$ at the reaction temperature of 250° C. The results are shown in Table 14 below.

TABLE 14

|  | CO only | 7% (by volume) of $H_2$ added | 14% of $H_2$ added | 20% of $H_2$ added | 25% of $H_2$ added |
| --- | --- | --- | --- | --- | --- |
| Methanol conversion (%) | 99.9 | 99.8 | 100 | 99.9 | 100 |
| Yield of acetic acid (%) | 85.1 | 97.3 | 95.1 | 92.9 | 92.1 |

As can be seen from Table 14, when a certain amount of hydrogen is mixed with the carbon monoxide under certain reaction conditions, the yield of acetic acid can be enhanced.

EXAMPLE 16

$RhCl_3.3H_2O$ and LiI were supported on active carbon in an aqueous phase in such a manner that 0.6% by weight of Rh based on the amount of the active carbon and 200mol % of LiI based on the amount of Rh were contained thereon. The resultant was then calcined at 300° C. to prepare the catalyst.

Using the catalyst obtained, this Example was carried out as described in Example 15 except that the GHSV of methanol was maintained at 3000 $hr^{-1}$. The results are shown in Table 15 below.

TABLE 15

|  | CO only | 7% of $H_2$ added |
| --- | --- | --- |
| Methanol conversion (%) | 86.2 | 100 |
| Yield of acetic acid (%) | 21.6 | 65.9 |
| Yield of methyl acetate (%) | 64.4 | 31.0 |

EXAMPLE 17

This Example was carried out as described in Example 15, except that a catalyst supported on active carbon and containing 0.6% by weight of Rh based on the active carbon and mol % of KCl based on the Rh was employed, and the GHSV of methanol was maintained at 2000$hr^{-1}$. The results are shown in Table 16 below.

TABLE 16

|  | CO only | 7% of $H_2$ added |
| --- | --- | --- |
| Methanol conversion (%) | 86.9 | 100 |
| Yield of acetic acid (%) | 22.5 | 46.1 |
| Yield of methyl acetate (%) | 60.4 | 50.1 |

EXAMPLE 18

$RhCl_3.3H_2O$ and $PdCl_2$ were supported on an active carbon in an aqueous phase in such a manner that 0.6% by weight of Rh based on the amount of the active carbon and 50mol % of $PdCl_2$ based on the amount of rhodium were contained thereon. The resulting mixture was then calcined at 300° C. to prepare the catalyst.

Using the catalyst obtained, this Example was carried out as described in Example 15 except that the GHSV of methanol was maintained at 1000 $hr^{-1}$. The results are shown in Table 17 below.

TABLE 17

|  | CO only | 7% of $H_2$ added |
| --- | --- | --- |
| Methanol conversion (%) | 100 | 100 |
| Yield of acetic acid (%) | 55.6 | 75.2 |
| Yield of methyl acetate (%) | 40.6 | 21.9 |

EXAMPLE 19

This Example was carried out as described in Example 15, except that a catalyst supported on active carbon, and containing 0.6% by weight of rhodium based on the active carbon and 50 mol % of $RuCl_3$ based on the rhodium was employed and the GHSV of methanol was maintained at 2,000 $hr^{-1}$. The results are shown in Table 18 below.

TABLE 18

|  | CO only | 7% of $H_2$ added |
| --- | --- | --- |
| Methanol conversion (%) | 93.9 | 100 |
| Yield of acetic acid (%) | 25.6 | 73.1 |
| Yield of methyl acetate (%) | 60.1 | 21.9 |

EXAMPLE 20

This Example was carried out as described in Example 2 except that a catalyst supported on active carbon and containing 0.6% by weight of Rh based on the active carbon and 50 mol % of Mn based on the Rh was employed, and the reaction temperature was changed to 270° C., in addition to the different values of GHSV. The results are shown in Table 19 below.

TABLE 19

| GHSV ($hr^{-1}$) | 1918 | 3417 | 4722 | 5754 |
| --- | --- | --- | --- | --- |
| Methanol conversion (%) | 100 | 99.8 | 95.8 | 90.7 |
| Yield of acetic acid (%) | 82.6 | 56.8 | 39.9 | 28.1 |
| Yield of methyl acetate (%) | 16.9 | 34.4 | 51.0 | 59.3 |

EXAMPLE 21

This Example was carried out as described in Example 2 except that a catalyst supported on active carbon and containing 0.6% by weight of Rh based on the active carbon and 25 mol % of Mn and 100 mol % of Li based on the Rh was employed, and the reaction temperature was changed to 270° C., in addition to the changed values of GHSV. The results are shown in Table 20 below.

TABLE 20

| GHSV (hr⁻¹) | 2278 | 3476 | 4856 | 6235 |
|---|---|---|---|---|
| Methanol conversion (%) | 100 | 100 | 96.9 | 88.5 |
| Yield of acetic acid (%) | 87.7 | 71.7 | 53.9 | 35.8 |
| Yield of methyl acetate (%) | 4.7 | 17.7 | 31.5 | 38.1 |

EXAMPLE 22

This Example was carried out as described in Example 2 except that a catalyst supported on active carbon and containing 0.6% by weight of Rh based on the active carbon and 50 mol % of Os based on the Rh was employed, and the reaction temperature was changed to 270° C., with the different values of GHSV. The results are shown in Table 21 below.

TABLE 21

| GHSV (hr⁻¹) | 2278 | 3596 | 4856 | 6115 |
|---|---|---|---|---|
| Methanol conversion (%) | 99.1 | 97.7 | 93.0 | 85.3 |
| Yield of acetic acid (%) | 58.7 | 37.0 | 22.7 | 16.8 |
| Yield of methyl acetate (%) | 30.2 | 52.4 | 61.8 | 62.7 |

EXAMPLE 23

This Example was carried out as described in Example 2, except that a catalyst supported on active carbon and containing 1.8% by weight of Rh based on the active carbon and 400 mol % of LiI based on the Rh was employed; the reaction temperature and the pressure were changed to 250° C. and 200 psi, respectively; and the GHSV of methanol was maintained at 1800 hr⁻¹, while adding various amounts of methyl acetate to the feed stream of methanol. The results are shown in Table 22.

TABLE 22

| Amount of methyl acetate added (mol %) | 0 | 5* | 10* |
|---|---|---|---|
| Methanol conversion (%) | 100 | 100 | 100 |
| Yield of acetic acid (%) | 80.2 | 93.4 | 99.9 |
| Yield of methyl acetate (%) | 18.8 | 16.0 | 20.1 |
| Total | 100 | 110* | 120* |

*1 mol % of methyl acetate added to the reaction system is counted as 2 mol % of methyl acetate as yielded from the reaction system in accordance with the second formula given on page 28 hereof. The same holds true with respect to the data shown in Tables 23 to 26 hereof.

EXAMPLE 24

This Example was carried out as described in Example 20 except that methyl acetate was added to the reactant mixture in 10 mol % based on the methanol used, in addition to the varied values of GHSV. The results are shown in Table 23 below.

TABLE 23

| GHSV (hr⁻¹) | 2027 | 3212 | 4395 | 5749 |
|---|---|---|---|---|
| Methanol conversion (%) | 99.4 | 99.5 | 98.2 | 95.5 |
| Yield of acetic acid (%) | 90.0 | 71.1 | 53.0 | 39.1 |
| Yield of methl acetate (%) | 26.7 | 41.8 | 57.6 | 70.2 |

EXAMPLE 25

This Example was carried out as described in Example 21 except that methyl acetate was added to the reactant mixture in 10 mol % based on the methanol used, in addition to the different values of GHSV. The results are shown in Table 24 below.

TABLE 24

| GHSV (hr⁻¹) | 2113 | 3212 | 4565 | 5748 |
|---|---|---|---|---|
| Methanol conversion (%) | 100 | 100 | 100 | 96.6 |
| Yield of acetic acid (%) | 98.3 | 85.5 | 72.8 | 53.7 |
| Yield of methl acetate (%) | 13.0 | 26.0 | 23.4 | 35.0 |

EXAMPLE 26

This Example was carried out as described in Example 22 except that methyl acetate was added to the reactant mixture in 10 mol % based on the methanol used, with the different values of GHSV. The results are shown in Table 25 below.

TABLE 25

| GHSV (hr⁻¹) | 2027 | 3212 | 4517 |
|---|---|---|---|
| Methanol conversion (%) | 100 | 98.8 | 95.4 |
| Yield of acetic acid (%) | 69.0 | 44.2 | 28.7 |
| Yield of methl acetate (%) | 38.8 | 64.4 | 77.0 |

As can be seen from Tables 22 to 25, when methanol is introduced together with an appropriate amount of methyl acetate, the yield of acetic acid can be enhanced significantly. Accordingly, if an appropriate amount of the methyl acetate produced by the carbonylation is recycled to the carbonylation reactor, the yield of acetic acid can be increased substantially.

EXAMPLE 27

This Example was carried out as described in Example 23 except that various amounts of water were added to the methanol feed containing 10 mol % of methyl acetate. The results are shown in Table 26.

TABLE 26

| Amount of water (mol %) | 0 | 10 | 20 |
|---|---|---|---|
| Methanol conversion (%) | 99.9 | 100 | 100 |
| Yield of acetic acid (%) | 99.8 | 111.9 | 114.3 |
| Yield of methyl acetate (%) | 19.9 | 8.1 | 5.7 |

TABLE 26-continued

| Amount of water (mol %) | 0 | 10 | 20 |
|---|---|---|---|
| Total | 120 | 120 | 120 |

As can be seen from Table 26, when water is added to the reactants, the yield of acetic acid can be enhanced.

EXAMPLE 28

To the same reactor containing the same catalyst as in Example 2, methyl acetate and $CH_3I$ in a molar ratio of 10:1 were introduced into the reactor. Thereafter, carbon monoxide was introduced into the reactor for the gas phase carbonylation thereof at a temperature of 250° C. and a pressure of 200 psi. The results are shown in Table 27 below.

TABLE 27

| GHSV $(hr^{-1})$* | 150 | 300 | 500 | 650 |
|---|---|---|---|---|
| Methyl acetate conversion (%) | 32.1 | 28.0 | 24.9 | 20.2 |
| Selectivity to acetic anhydride (%) | 98.2 | 98.1 | 97.8 | 98.1 |

*GHSV of methyl acetate

EXAMPLE 29

This Example was carried out in the same manner as described in Example 28, except that the catalyst prepared as in Example 10 was employed, with the changes made in the GHSV of methyl acetate. The results are shown in Table 28 below.

TABLE 28

| GHSV $(hr^{-1})$ | 150 | 330 | 500 | 670 |
|---|---|---|---|---|
| Methyl acetate conversion (%) | 32.0 | 26.1 | 23.9 | 22.2 |
| Selectivity to acetic anhydride (%) | 99.1 | 97.7 | 98.1 | 98.1 |

EXAMPLE 30

This Example was carried out in the same manner as described in Example 28, except that the catalyst prepared as in Example 6 was employed; and the GHSV of methyl acetate was maintained at 500 $hr^{-1}$, while varying the reaction temperature. The results are shown in Table 29 below.

TABLE 29

| Temperature (°C.) | 240 | 250 | 260 |
|---|---|---|---|
| Methyl acetate conversion (%) | 28.1 | 25.9 | 21.0 |
| Selectivity to acetic anhydride (%) | 98.2 | 97.1 | 97.9 |

EXAMPLE 31

Methyl acetate was carbonylated to form acetic anhydride in a liquid phase reaction as follows. A 50 ml autoclave made of Hastalloy equipped with a magne-drive type stirrer was used as the carbonylation reactor. The reactor was charged with a reaction mixture comprised of approximately 93.5 mol % methyl acetate, 2.25 mol % methyl iodide, 4 mol % of lithium iodide (LiI) as a promotor and 0.25 mol % rhodium acetate. This mixture was kept under the reaction conditions of 170° C. and CO partial pressure of 300 psi(total pressure being 500 psi) for 3 hrs. The acetic anhydride yield was more than 95% based on the methyl acetate.

EXAMPLE 32

This Example was carried out as described in Example 31, except that the reaction time was changed to 2 hrs while employing LiI, LiOAc, LiCl and PPNI($Ph_3P=N^+=PPh_3I^-$) as the promoter, respectively, in order to compare their effectiveness. The conversion rates of methyl acetate to acetic anhydride are shown in Table 30 provided below.

TABLE 30

| Promotor | LiOAc | LiI | LiCl | PPNI |
|---|---|---|---|---|
| Methyl acetate conversion (%) | 90.0 | 87.9 | 85.2 | 84.8 |

EXAMPLE 33

This Example was carried out as described in Example 31, except that LiI was not added and, instead, zirconyl diacetate (200 mol % to rhodium) and a tetraammonium salt, i.e., tetraethylammonium iodide (2000 mol % to rhodium) were added as promoters; and the reaction was conducted at 165° C. and 800 psi for 2 hrs. The yield of acetic anhydride was about 90%.

EXAMPLE 34

This Example was carried out as described in Example 31, except that LiI was not added and, instead, triphenyl phosphine ligand (500 mol % to rhodium) was added, and the reaction was conducted at 160° C. and 1000 psi for 2 hrs. The yield of acetic anhydride was 88%.

While the invention has been described in connection with the above specific embodiments, it should be recognized that various modifications and changes as may be apparent to those skilled in the art to which the invention pertains may be made and also fall within the scope of the invention as defined by the claims that follow.

What is claimed is:

1. A process for treating an industrial gas containing metallic carbonyl compounds which comprises contacting said industrial gas with iodine vapor to thereby convert the metallic carbonyl compounds to one or more than one metallic iodide.

2. The process of claim 1, wherein the industrial gas is carbon monoxide or synthesis gas.

3. The process of claim 2, wherein the iodine is employed in an amount ranging from 1 to 10 times the molar amount of the metallic compounds contained in the industrial gas.

4. The process of claim 3, which further comprises passing the industrial gas treated with the iodine through an adsorption column provided with an adsorbent to remove the metallic iodide.

5. The process of claim 4, wherein the adsorbent is selected from the group consisting of active carbon, clay, alumina, silica, silica-alumina and zeolite.

6. A process for the selective production of acetic acid, which comprises:
  (a) pretreating carbon monoxide by passing it through an adsorption column provided with an adsorbent;
  (b) carbonylating methanol in a gas phase with said pretreated carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst to provide a mixture of acetic acid in a major amount and methyl acetate in a minor amount;
  (c) separating said methyl acetate in the minor amount and the co-catalyst and recycling the separated methyl acetate and the co-catalyst to the carbonylation reactor; and
  (d) recovering from the mixture said acetic acid in the major amount.

7. The process of claim 6, wherein said carbon monoxide is treated with a halogen prior to its passing through the adsorption column.

8. The process of claim 7, wherein said rhodium compound is selected from the group consisting of $RhX_3$, $RhX_3 \cdot 3H_2O$, $Rh_2(CO)_4X_2$, Y, $Rh_2(CO)_8$, $Rh(NO_3)_3$, Y, $Rh_2O_3$, $Rh(CH_3COO)_3$, $_2$, $Rh_2(CO)X$, Rh metal, $RhX_2(CH_3X)_2$, $Rh(SnX_3)_3$, $RhX(CO)_2$, $(R_4Z)_2$, $(R_4Z)_2$, $RhX_3$, $RhXH_2$, $_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group.

9. The process of claim 7, wherein said alkali metal is selected from the group consisting of Li, Na, K, Rb, Cs and Fr.

10. The process of claim 7, wherein said alkaline earth metal is selected from the group consisting of Be, Mg, Ca, Sr, Ba and Ra.

11. The process of claim 7, wherein said transition metal is selected from the group consisting of Co, Ru, Pd, Pt, Os, It, Ni, Mn, Re, Cr, Mo, W, V, Nb, Ta, Ti, Zr and Hr.

12. The process of claim 7, wherein said co-catalyst is selected from the group consisting of $CH_3I$, $CH_3Br$, $CH_3Cl$, $I_2$, $Br_2$, $Cl_2$, HI, HBF and HCl.

13. The process of claim 7, wherein said hydrogen is added to said carbon monoxide in an amount of up to 50 mol % based on the amount of said carbon monoxide.

14. The process of claim 7, wherein water is introduced into the carbonylation reactor in an amount of up to 20 mol % based on the amount of said methanol.

15. The process of claim 7, wherein said carbonylation is carried out at a temperature ranging from 200° to 280° C., at a pressure ranging from 10 to 20 atm, and at a GHSV of the methanol ranging from 300 to 5,000hr$^{-1}$.

16. A process for selectively producing methyl acetate, which comprises:
  (a) pretreating carbon monoxide by passing it through an adsorption column provided with an adsorbent;
  (b) carbonylating methanol in a gas phase with said pretreated carbon monoxide in a carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under milder carbonylation conditions and a higher GHSV of methanol to produce a mixture of acetic acid and methyl acetate;
  (c) separating from the production mixture in a distillation column the acetic acid as a high boiling fraction thereof, a mixture of the co-catalyst and a minor portion of the methyl acetate as a low boiling fraction thereof, and the remaining major portion of the methyl acetate as an intermediate boiling fraction thereof;
  (d) recycling the separated mixture of the co-catalyst and the minor portion of the methyl acetate to the carbonylation reactor; and
  (e) recovering the acetic acid and the remaining major portion of the methyl acetate, respectively.

17. The process of claim 16, wherein said carbon monoxide is treated with a halogen prior to its passing through the adsorption column.

18. The process of claim 17, wherein said rhodium compound is selected from the group consisting of $RhX_3$, $RhX_3 \cdot 3H_2O$, $Rh_2(CO)_4X_2$, Y, $Rh_2(CO)_8$, $Rh(NO_3)_3$, Y, $Rh_2O_3$, $Rh(CH_3COO)_3$, $_2$, $Rh_2(CO)X$, Rh metal, $RhX_2(CH_3X)_2$, $Rh(SnX_3)_3$, $RhX(CO)_2$, $(R_4Z)_2$, $(R_4Z)_2$, $RhX_3$, $RhXH_2$, $_3Rh(CO)H$ and $Y_4Rh_2X_2(SnX_3)_4$ wherein X is Cl Br or I; Y is Na, Li oF K; Z is N, As or P; Q is As, P or Sb; and R is a $C_1$ to $C_{12}$ alkyl or aryl group.

19. The process of claim 17, wherein said alkali metal is selected from the group consisting of Li, Na, K, Rb, Cs and Fr.

20. The process of claim 17, wherein said alkaline earth metal is selected from the group consisting of Be, Mg, Ca, St, Ba and Ra.

21. The process of claim 17, wherein said transition metal is selected from the group consisting of Co, Ru, Pd, Os, It, Ni, Mn, Re, Cr, Mo, W, V, Nb, Ta, Ti, Zr and Hr.

22. The process of claim 17, wherein said co-catalyst is selected from the group consisting of $CH_3I$, $CH_3BF$, $CH_3Cl$, $I_2$, $BF_2$, $Cl_2$, HI, HBr and HCl.

23. The process of claim 22, wherein said co-catalyst is $CH_3I$.

24. The process of claim 23, wherein said mixture of the co-catalyst and the minor portion of the methyl acetate is an azeotrope thereof.

25. The process of claim 17, wherein said hydrogen is added to said carbon monoxide in an amount of up to 50 mol % based on the amount of said carbon monoxide.

26. The process of claim 17, wherein said carbonylation is carried out at a temperature ranging from 150° to 270° C., at a pressure ranging from 8 to 15 atm, and at a GHSV of the methanol ranging from 1,000 to 10,000hr$^{-1}$.

27. A process for producing acetic anhydride, which comprises:
  (a) pretreating carbon monoxide by passing it through an adsorption column provided with an adsorbent;
  (b) carbonylating methanol in a gas phase with said pretreated carbon monoxide in a first carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under milder carbonylation conditions and at a higher GHSV of methanol to produce a mixture of acetic acid and methyl acetate;
  (c) separating from the production mixture in a distillation column the acetic acid as a high boiling fraction thereof, and a mixture of the co-catalyst and the methyl acetate as a low boiling fraction thereof;

(d) removing, optionally, a portion of the co-catalyst from the low boiling fraction and recycling it to the first carbonylation reactor;

(e) introducing the methyl acetate and all or the remaining portion of the co-catalyst into a second carbonylation reactor;

(f) carbonylating the methyl acetate in a gas phase with said pretreated carbon monoxide in the second carbonylation reactor, said carbon monoxide being optionally in admixture of hydrogen, in the presence of the rhodium catalyst and the co-catalyst to provide a mixture containing acetic anhydride;

(g) separating in a distillation column the acetic anhydride as a heavy boiling fraction thereof and separating the co-catalyst and unreacted methyl acetate as a light boiling fraction thereof;

(h) recycling the separated co-catalyst and the unreacted methyl acetate to the first carbonylation reactor; and (i) recovering the separated acetic anhydride.

28. The process of claim 27, wherein each of said carbon monoxide is treated with a halogen prior to its passing through the adsorption column, respectively.

29. The process of claim 28, wherein said rhodium compound is selected from the group consisting of $RhX_3$, $RhX_3.3H_2O$, $Rh_2(CO)_4X_2$, Y, $Rh_2(CO)_8$, $Rh(NO_3)_3$, Y, $Rh_2O_3$, $Rh(CH_3COO)_3$, $_2$, $Rh_2(CO)X$, Rh metal, $RhX_2(CH_3X)_2$, $Rh(SnX_3)_3$, $RhX(CO)_2$, $(R_4Z)_2$, $(R_4Z)_2$, $RhX_3$, $RhXH_2$, $_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group.

30. The process of claim 28, wherein said alkali metal is selected from the group consisting of Li, Na, K, Rb, Cs and Fr.

31. The process of claim 28, wherein said alkaline earth metal is selected from the group consisting of Be, Mg, Ca, Sr, Ba and Ra.

32. The process of claim 28, wherein said transition metal is selected from the group consisting of Co, Ru, Pd, Pt, Os, Ir, Ni, Mn, Re, Cr, Mo, W, V, Nb, Ta, Ti, Zr and Hr.

33. The process of claim 28, wherein said co-catalyst is selected from the group consisting of $CH_3I$, $CH_3Br$, $CH_3Cl$, $I_2$, $BF_2$, $Cl_2$, HI, HBr and HCl.

34. The process of claim 28, wherein said first carbonylation in step(a) is carried out at a temperature ranging from 150° to 280° C., at a pressure ranging from 8 to 15 atm, and at a GHSV of methanol ranging from 1,000 to 10,000 $hr^{-1}$.

35. The process of claim 28, wherein said second carbonylation in step(e) is carried out at a temperature ranging from 200° to 280° C., at a pressure ranging from 10 to 20 atm, and at a GHSV of methyl acetate ranging from 100 to 2000 $hr^{-1}$.

36. The process of claim 28, wherein said co-catalyst is $CH_3I$.

37. A process for producing acetic anhydride, which comprises:

(a) pretreating carbon monoxide by passing it through an adsorption column provided with an adsorbent;

(b) carbonylating methanol in a gas phase with said pretreated carbon monoxide in a first carbonylation reactor, said carbon monoxide being optionally in admixture of hydrogen, in the presence of a rhodium catalyst comprised of a rhodium compound and a second metallic component selected from the group consisting of an alkali metal, an alkaline earth metal, a transition metal and a mixture thereof, and supported on an inert material, and a halide co-catalyst under milder carbonylation conditions and at a higher GHSV of methanol to produce a mixture of acetic acid and methyl acetate;

(c) separating from the production mixture in a distillation column the acetic acid as a high boiling fraction thereof, and a mixture of the co-catalyst and the methyl acetate as a low boiling fraction thereof;

(d) removing, optionally, a portion of the co-catalyst from the low boiling fraction and recycling it to the first carbonylation reactor;

(e) introducing the methyl acetate and all or the remaining portion of the co-catalyst into a second carbonylation reactor;

(f) carbonylating the methyl acetate in a liquid phase with said pretreated carbon monoxide in the second carbonylation reactor in the presence of a rhodium catalyst, and a promoter and/or a ligand to produce a mixture containing acetic anhydride;

(g) separating the mixture obtained in said step (f) in a distillation column into an overhead fraction containing the co-catalyst and any unreacted methyl acetate; an intermediate fraction containing said acetic anhydride; and a liquid residue containing the catalyst, the promoter and/or the ligand;

(h) recycling the overhead fraction containing the co-catalyst and the unreacted methyl acetate to the first carbonylation reactor, and recycling the liquid residue containing the catalyst, the promoter and/or the ligand to the second carbonylation reactor; and (i) recovering said acetic anhydride from the intermediate fraction.

38. The process of claim 37, wherein each of said carbon monoxide is treated with a halogen prior to its passing through the adsorption column, respectively.

39. The process of claim 37, wherein said rhodium compound employed in said step(a) is selected from the group consisting of $RhX_3$, $RhX_3.3H_2O$, $Rh_2(CO)_4X_2$, Y, $Rh_2(CO)_8$, $Rh(NO_3)_3$, Y, $Rh_2O_3$, $Rh(CH_3COO)_3$, $_2$, $Rh_2(CO)X$, Rh metal, $RhX_2(CH_3X)_2$, $Rh(SnX_3)_3$, $RhX(CO—_2$, $(R_4Z)_2$, $(R_4Z)_2$, $RhX_3$, $RhXH_2$, $_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group.

40. The process of claim 38, wherein said alkali metal is selected from the group consisting of Li, Na, K, Rb, Cs and Fr.

41. The process of claim 38, wherein said alkaline earth metal is selected from the group consisting of Be, MS, Ca, Sr, Ba and Ra.

42. The process of claim 38, wherein said transition metal is selected from the group consisting of Co, Ru, Pd, Pt, Os, It, Ni, Mn, Re, Cr, Mo, W, V, Nb, Ta, Ti, Zr and Hr.

43. The process of claim 38, wherein said co-catalyst is selected from the group consisting of $CH_3I$, $CH_3Br$, $CH_3Cl$, $I_2$, $Br_2$, $Cl_2$, HI, HBr and HCl.

44. The process of claim 43, wherein said co-catalyst is $CH_3I$.

45. The process of claim 38, wherein said catalyst employed in step(e) is an element of a compound of a Group VIII noble metal.

46. The process of claim 45, wherein said catalyst is a rhodium compound selected from the group consisting of $RhX_3$, $RhX_3.3H_2O$, $Rh_2(CO)_4X_2$, Y, $Rh_2(CO)_8$, $Rh(NO_3)_3$, Y, $Rh_2O_3$, $Rh(CH_3COO)_3$, $_2$, $Rh_2(CO)X$, Rh metal, $RhX_2(CH_3X)_2$, $Rh(SnX_3)_3$, $RhX(CO-)_2$, $(R_4Z)_2$, $(R_4Z)_2$ $RhX_3$, $RhXH_2$, $_3Rh(CO)H$, $Y_4Rh_2X_2(SnX_3)_4$, wherein X is Cl, Br or I; Y is Na, Li or K; Z is N, As or P; Q is As, P or Sb; and R is a $C_1$ to $C_{12}$ alkyl or aryl group.

47. The process of claim 38, wherein said promoter is an element or a compound of a member selected from the group consisting of organic cations, Group IA metals having an atomic weight greater than 5 and Groups IIA, IIIA and IVB metals, the non-noble metals of Group VIII, the lanthanide group metals and the actinide group metals.

48. The process of claim 47, wherein said element or said member is selected from the group consisting of Li, Mg, Ca, Ti, Cr, Fe, Ni, Zr and Al.

49. The process of claim 47, wherein said promoter is selected from the group consisting of LiI, LiOAc, LiCl, PPNI ($Ph_3P=N^+=PPh_3.I^-$), zirconyl diacetate and a tetraammonium salt.

50. The process of claim 38, wherein said ligand is selected from the group consisting of phosphine, amine, antimony and tin compound ligands.

51. The process of claim 38, wherein said carbonylation in step(a) is carried out at a temperature ranging from 150° to 270° C., at a pressure ranging from 8 to 15 atm, and at a GHSV of methanol ranging from 1,000 to 10,000 $hr^{-1}$.

52. The process of claim 38, wherein said carbonylation in step(e) is carried out at a temperature ranging from 150° to 200° C., and at a pressure ranging from 20 to 100 atm.

* * * * *